(12) United States Patent
He et al.

(10) Patent No.: US 7,101,428 B2
(45) Date of Patent: Sep. 5, 2006

(54) 2,9-DICHLORO-QUINACRIDONE AS ALPHA-QUINACRIDONE CRYSTAL PHASE INHIBITOR

(75) Inventors: Yingxia He, Wilmington, DE (US); Colin Campbell, Claymont, DE (US); Gordian Schilling, Newark, DE (US); Rhonda Carter, Bear, DE (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/988,227

(22) Filed: Nov. 12, 2004

(65) Prior Publication Data

US 2005/0183635 A1 Aug. 25, 2005

Related U.S. Application Data

(60) Provisional application No. 60/519,842, filed on Nov. 13, 2003.

(51) Int. Cl.
*C09B 48/00* (2006.01)
*C09D 11/00* (2006.01)

(52) U.S. Cl. ............... 106/495; 106/31.77; 106/497; 524/90; 544/49; 544/56

(58) Field of Classification Search ........... 106/495, 106/497, 31.77; 524/90; 544/49, 56
See application file for complete search history.

(56) References Cited

U.S. PATENT DOCUMENTS

| 2,844,484 A | 7/1958 | Reidinger et al. |
|---|---|---|
| 2,844,485 A | 7/1958 | Struve |
| 2,844,581 A | 7/1958 | Manger et al. |
| 2,969,366 A | 1/1961 | Griswold et al. |
| 4,857,646 A | 8/1989 | Jaffe ........................ 546/49 |
| 5,229,515 A | 7/1993 | Pfenninger et al. ........... 546/49 |
| 5,281,269 A | 1/1994 | Ganci et al. ................ 106/497 |
| 5,755,874 A | 5/1998 | Urban et al. ................ 106/497 |
| 5,989,333 A * | 11/1999 | Urban et al. ................ 106/495 |
| 6,312,512 B1 | 11/2001 | Urban et al. ................ 106/495 |

FOREIGN PATENT DOCUMENTS

EP 0517662 12/1992

OTHER PUBLICATIONS

W. Herbst et al., Industrial Organic Pigments, Production, Properties, Applications, 2nd Completely Revised Ed., (1997), p. 464, no month.
R. B. McKay, Control of the Application Performance of Classical Organic Pigments, JOCCA, (1989), pp. 89-93, no month.

* cited by examiner

Primary Examiner—Anthony J. Green
(74) Attorney, Agent, or Firm—Shiela A. Loggins

(57) ABSTRACT

The invention is directed to a method or use of 2,9-dichloroquinacridone as a crystal phase inhibitor during the beta-quinacridone or gamma-quinacridone crude pigment particle size reduction processes. 2,9-dichloroquinacridone is added to the milling composition of the crude gamma or crude beta quinacridone.

18 Claims, 12 Drawing Sheets

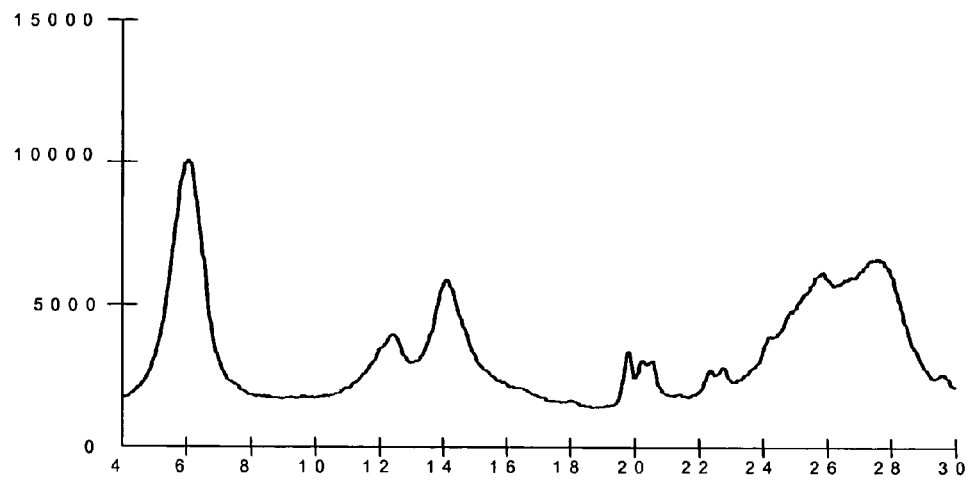
Figure 1. X-ray of pure alpha quinacridone generated from milling process
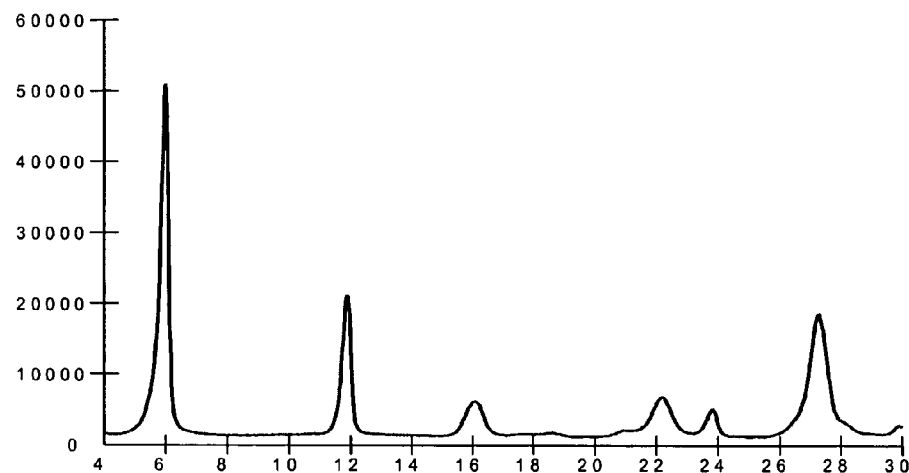
Figure 2. X-ray of pure beta-quinacridone

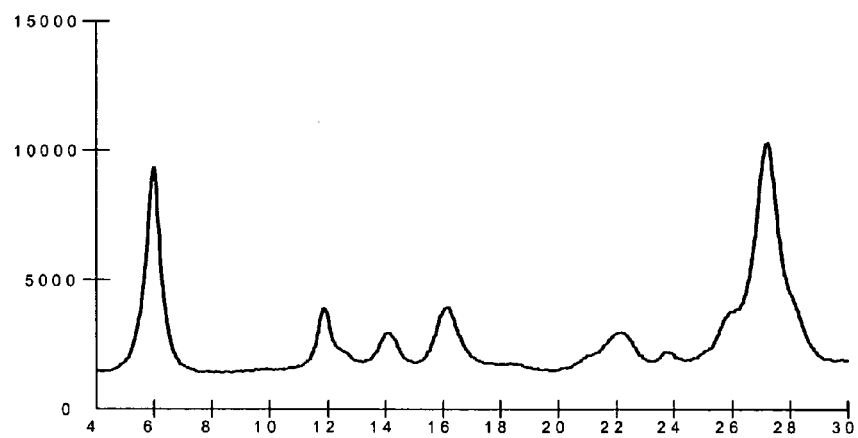
Figure 3. X-ray of example 1, aqueous wet-milled crude beta-quinacridone without 2,9-dichloroquinacridone.
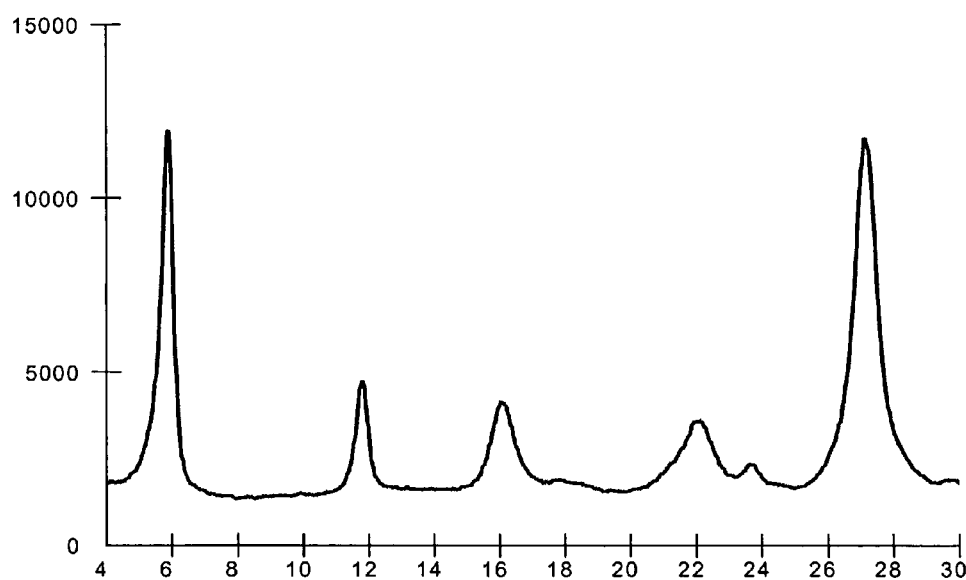
Figure 4. X-ray of example 2, aqueous wet-milled crude beta-quinacridone with 2,9-dichloroquinacriodone.

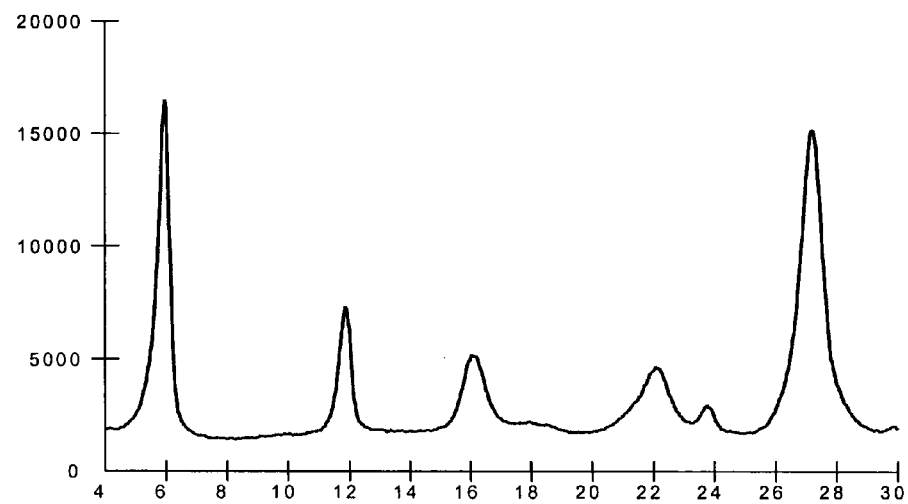
Figure 5. X-ray of example 3, aqueous wet-milled crude beta-quinacridone with 2,9-Cl$_2$QA
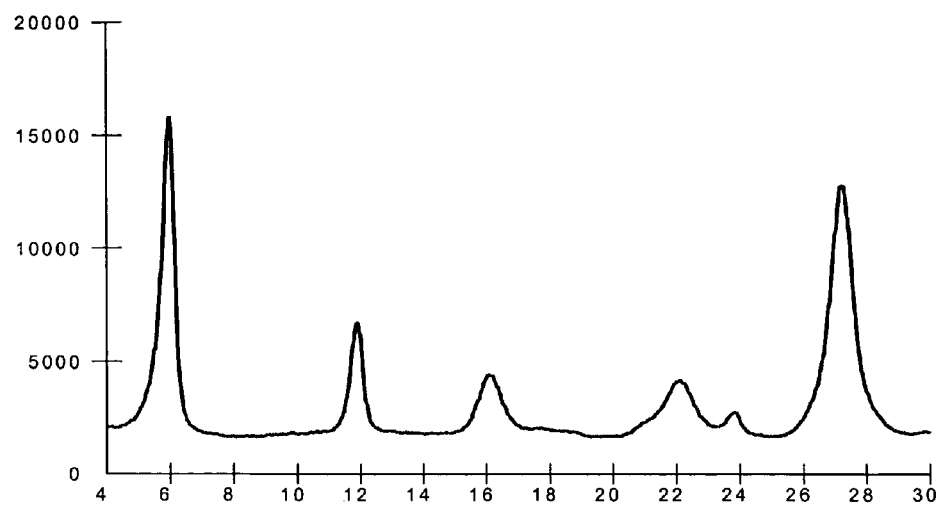
Figure 6. X-ray of example 4, aqueous wet-milled crude beta-quinacridone with 2,9-dichloroquinacridone.

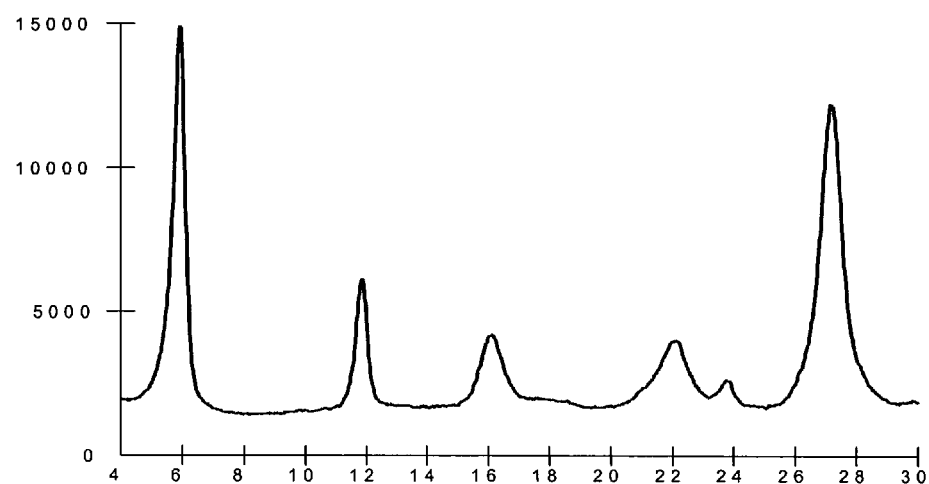
Figure 7. X-ray of example 5, aqueous wet-milled crude beta-quinacridone with 2,9-dichloroquinacrione.
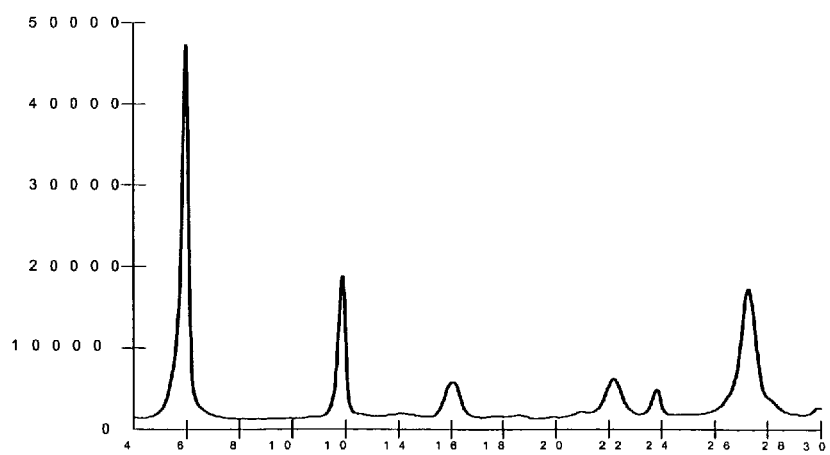
Figure 8. X-ray of comparison example 1

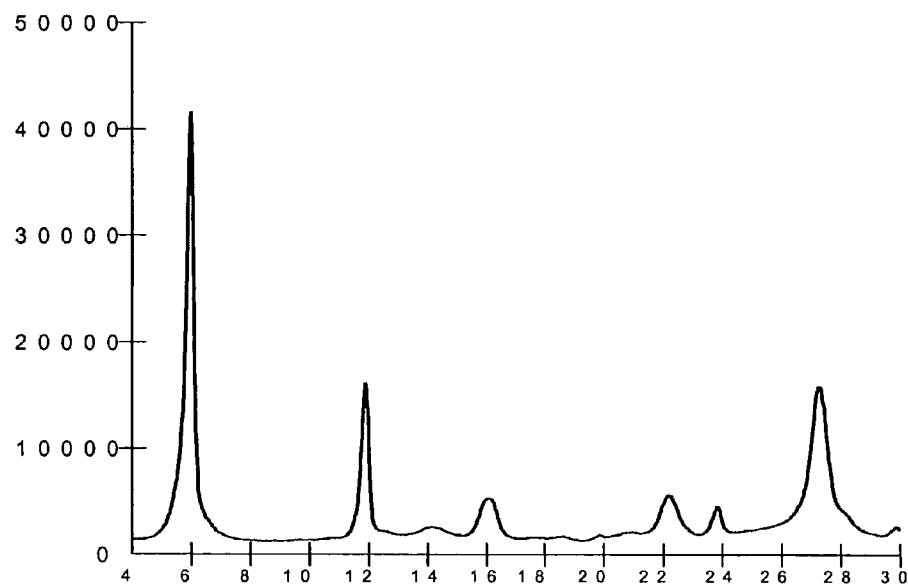
Figure 9. X-ray of comparison example 2.
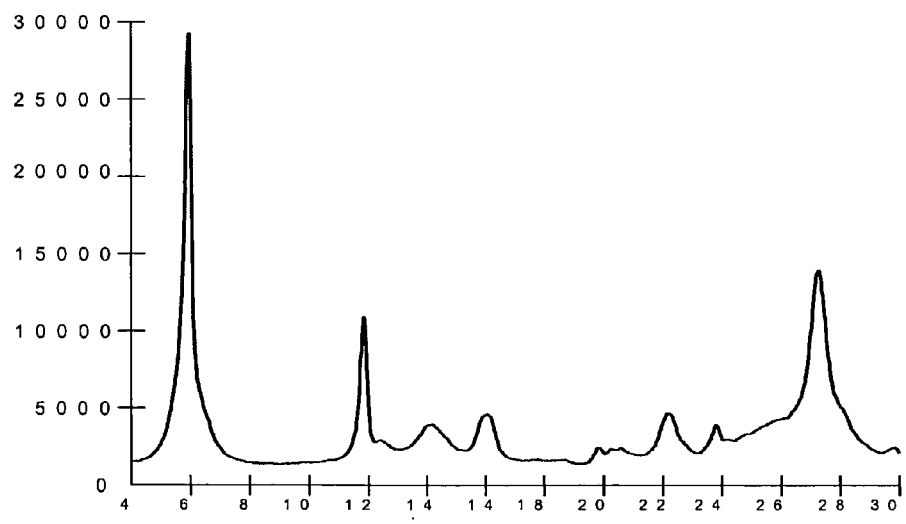
Figure 10. X-ray of comparison example 3.

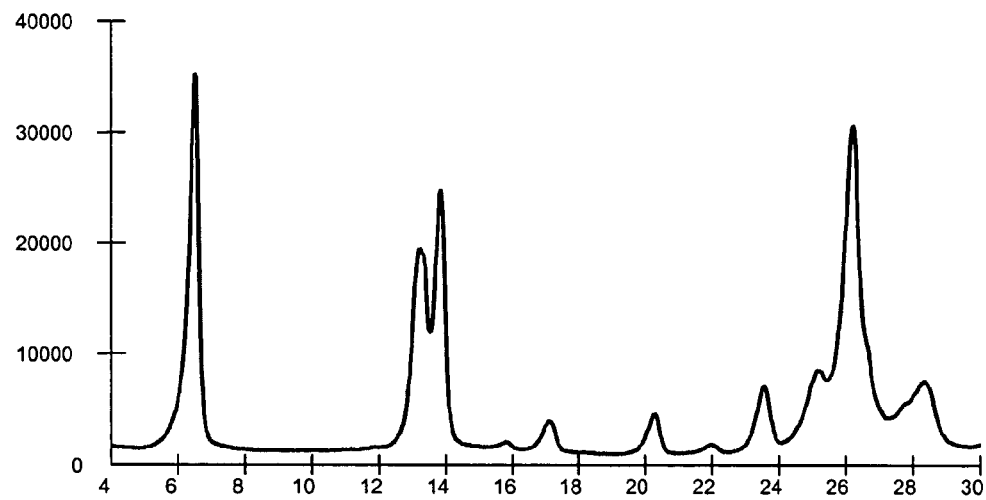
Figure 11. X-ray of unmilled gamma-quinacridone.
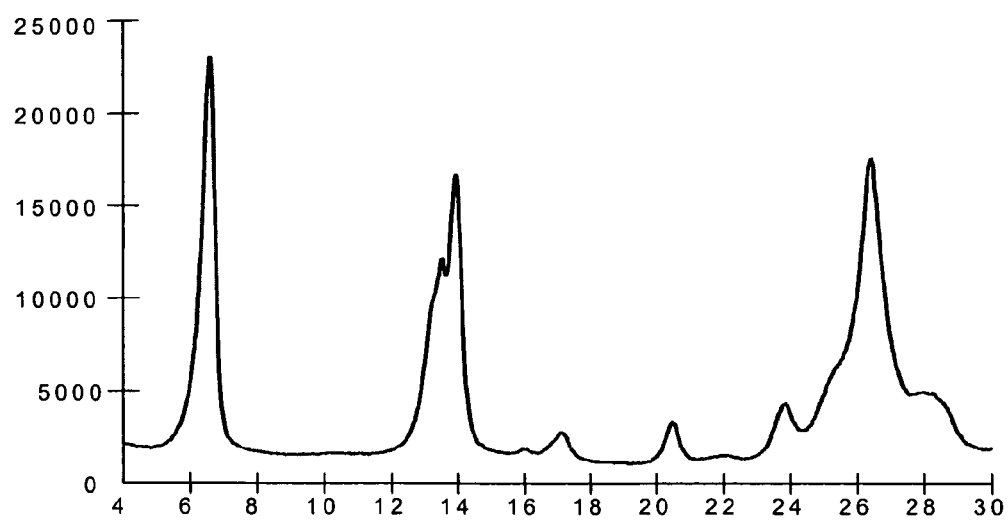
Figure 12. X-ray of wet-milled gamma crude for 12 minutes.

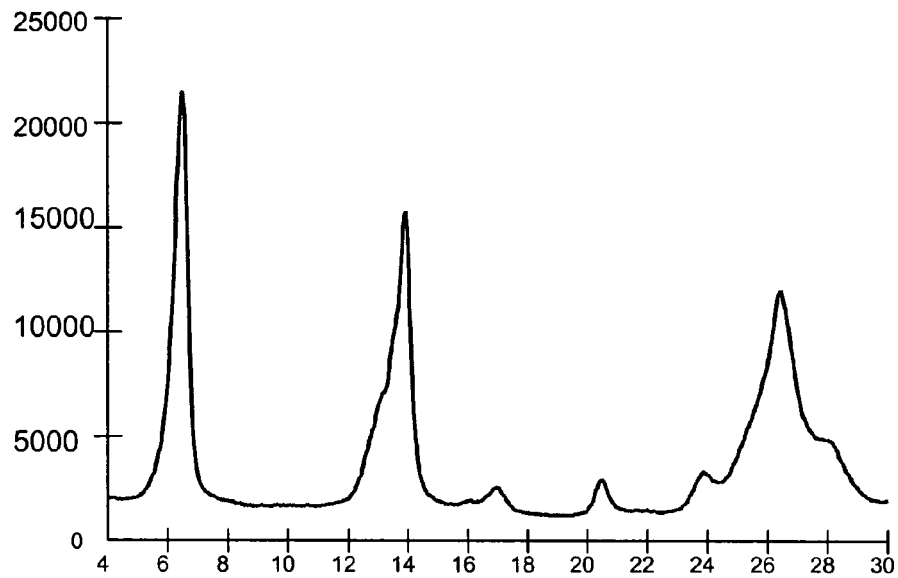
Figure 13. X-ray of wet-milled gamma crude of example 18 with 0.5 % 2,9-dichloroquinacridone for 30 minutes.
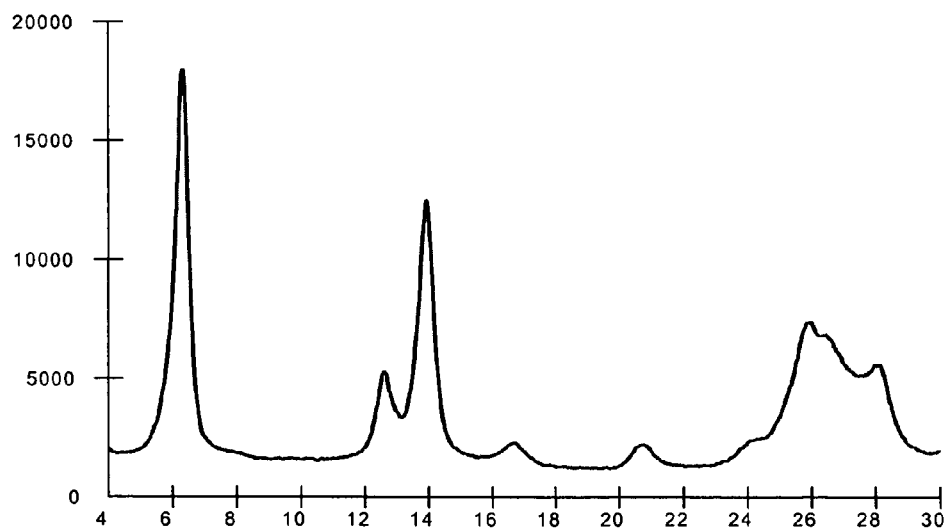
Figure 14. X-ray of wet-milled gamma crude of example 13 with 0.5 % 2,9-dichloroquinacridone for 60 minutes.

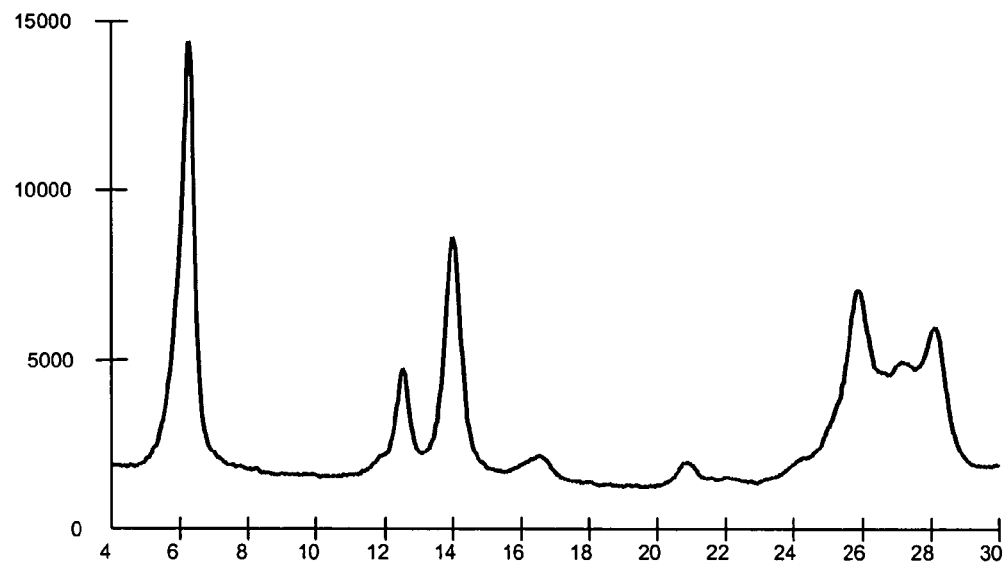
Figure 15. X-ray of wet-milled gamma crude of example 14 with 0.5 % 2,9-dichloroquinacridone for 90 minutes.
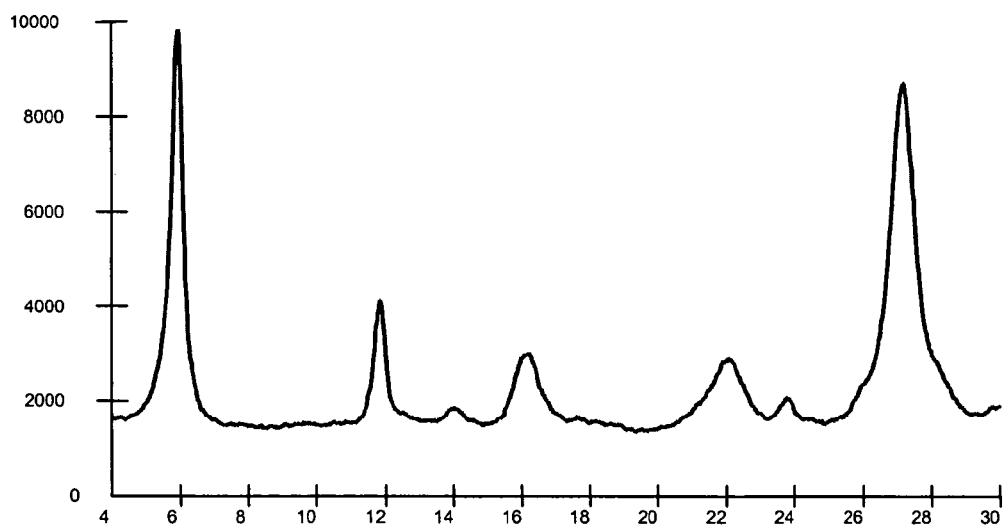
Figure 16. X-ray of wet-milled gamma crude of example 16 with 0.5 % 2,9-dichloroquinacridone for 120 minutes.

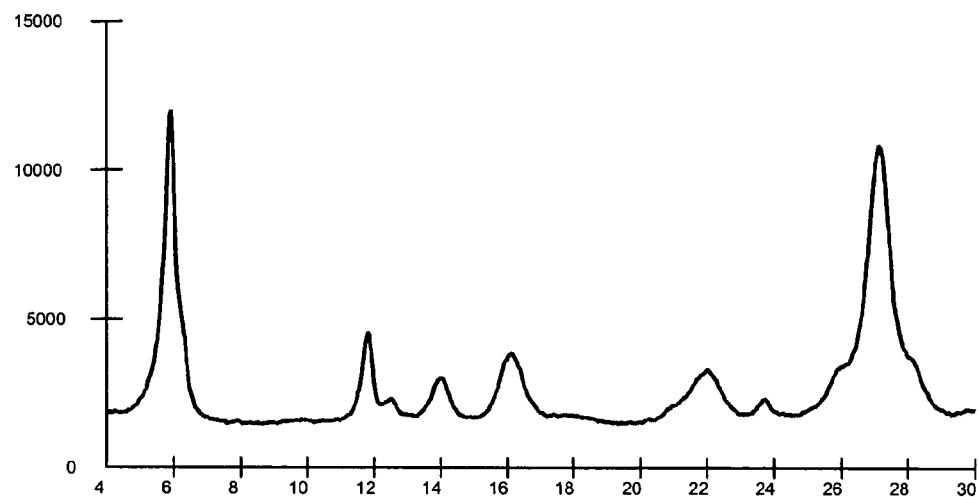
Figure 17. X-ray of wet-milled gamma crude of example 15 with 1.0 % 2,9-dichloroquinacridone for 120 minutes.
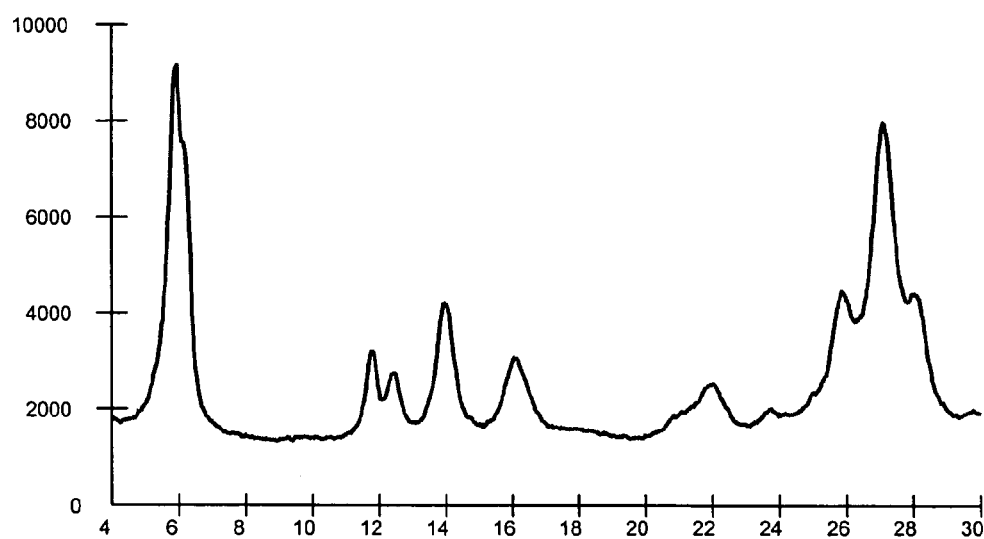
Figure 18. X-ray of wet-milled gamma crude of example 11 with 2.0 % 2,9-dichloroquinacridone for 120 minutes.

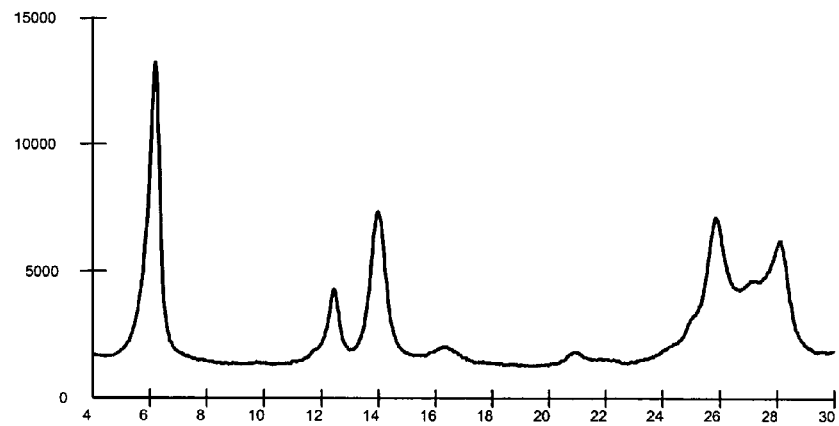
Figure 19. X-ray of wet-milled gamma crude of example 17 with 3.0 % 2,9-dichloroquinacridone for 120 minutes.
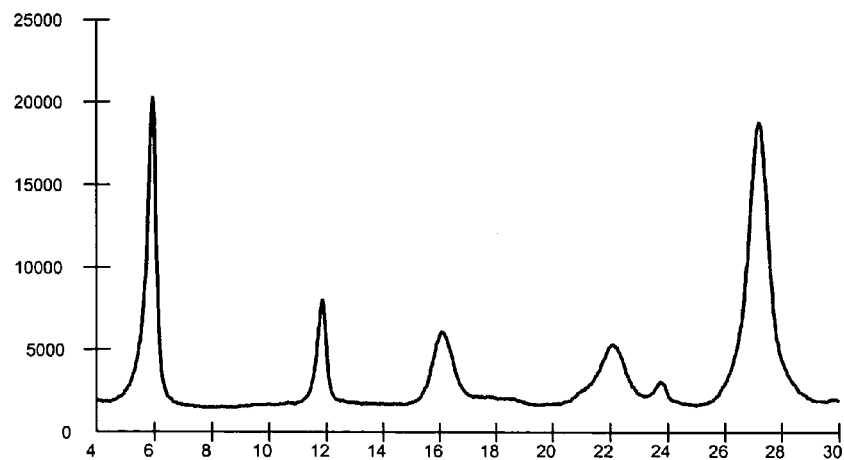
Figure 20. X-ray of wet-milled beta crude of example 6 with 0.5 % 2,9-dichloroquinacridone for 60 minutes.

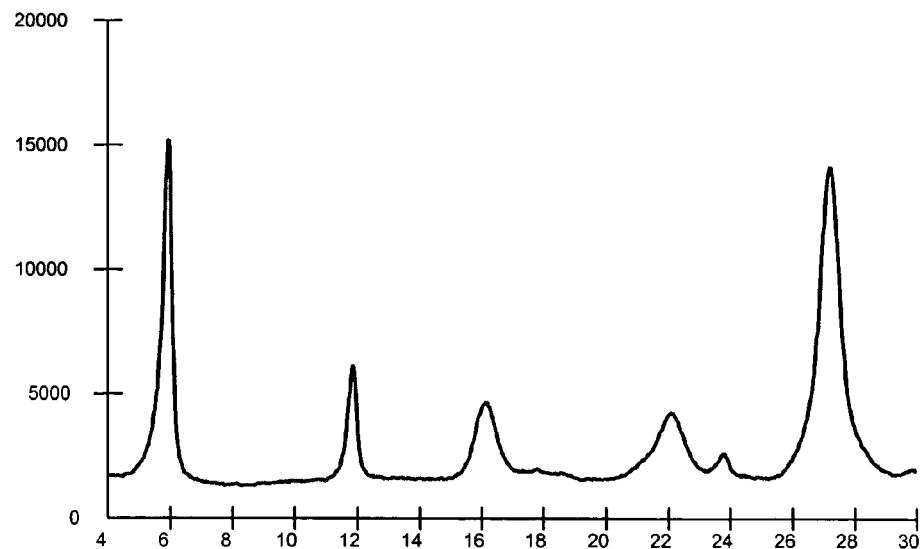
Figure 21. X-ray of wet-milled beta crude of example 7 with 0.5 % 2,9-dichloroquinacridone for 120 minutes.
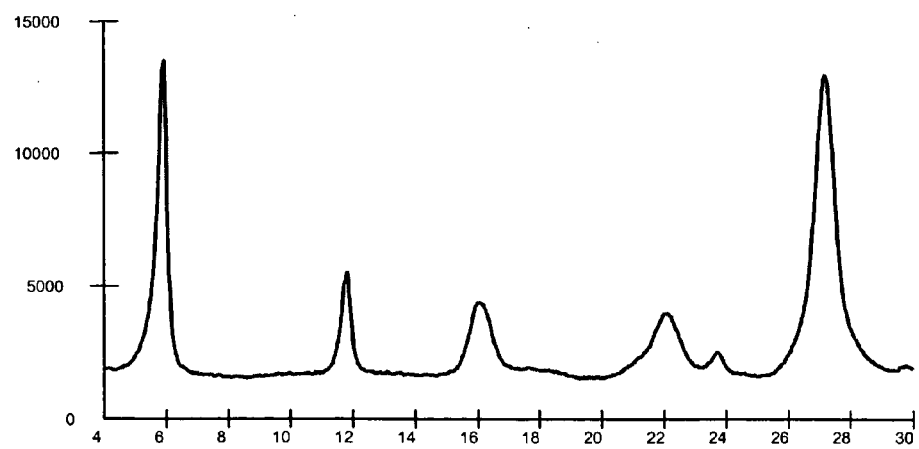
Figure 22. X-ray of wet-milled beta crude of example 8 with 1.0 % 2,9-dichloroquinacridone for 60 minutes.

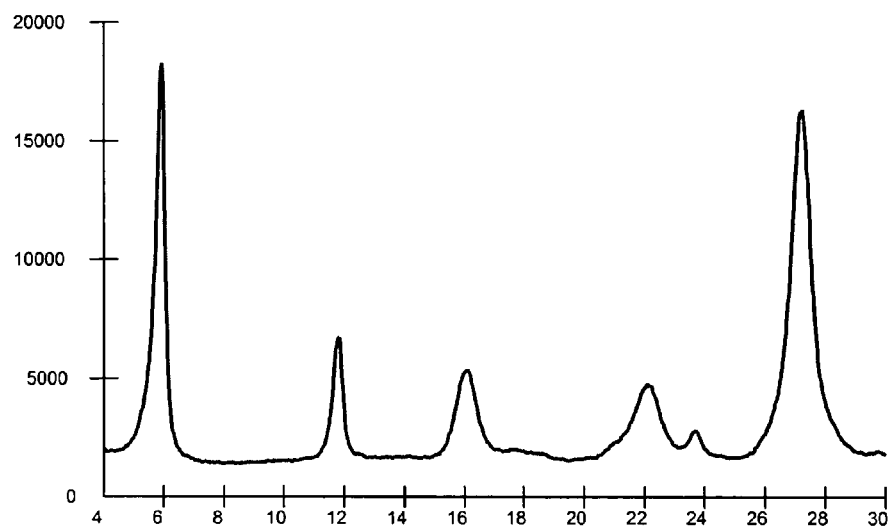
Figure 23. X-ray of wet-milled beta crude of example 9 with 1.0 % 2,9-dichloroquinacridone for 120 minutes.
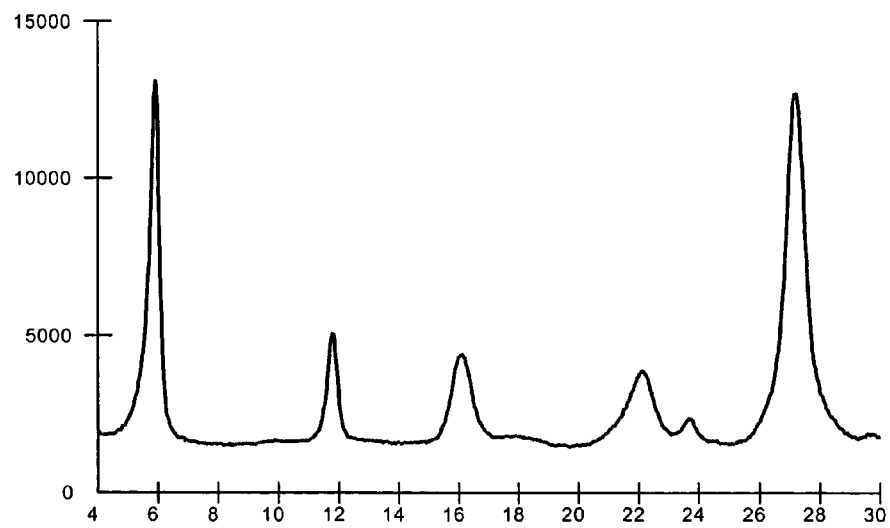
Figure 24. X-ray of wet-milled beta crude of example 10 with 2.0% 2,9-dichloroquinacridone for 60 minutes.

2,9-DICHLORO-QUINACRIDONE AS ALPHA-QUINACRIDONE CRYSTAL PHASE INHIBITOR

This application claims the benefit of U.S. Provisional application No. 60/519,842, filed Nov. 13, 2003.

SUMMARY OF INVENTION

The invention is directed to a method or use of 2,9-dichloro-quinacridone as a crystal phase inhibitor during the beta-quinacridone or gamma-quinacridone crude pigment particle size reduction processes.

BACKGROUND OF THE INVENTION

Quinacridone (QA) is known to exist in three crystal phases. The alpha phase, described in U.S. Pat. No. 2,844,484 and gamma phase described in U.S. Pat. Nos. 2,844,581 and 2,969,366 forms are a bluish red color. The beta form described in U.S. Pat. Nos. 2,844,485 and 4,857,646 is violet. The alpha quinacridone crystal form is not commercially valuable because it is not heat stable. See W. Herbst and K. Hunger, "Industrial Organic Pigments", VCH Publishers, Inc., 1997, page 464.

It is well known in the art that organic pigments, such as quinacridones, as synthesized, are generally unsuitable for use as pigments and must be further processed to develop the requisite pigmentary properties such as particle size, particle shape, polymorphic phase, and tinctorial strength.

In order to obtain the color properties required for a particular application, the pigment crude must be converted to a pigmentary grade with a proper tint strength, transparency or opacity for a particular application. The effectiveness of a given pigment type in imparting color is dependent upon it's particle size in dispersion. Thus, color strength, transparency and opacity are all properties that are highly dependant on particle size. Consequently, crude organic pigments undergo one or more finishing or conditioning steps that require particle size reduction. See, for example R. B. McKay, "Control of the Application Performance of Classical Organic Pigments" in JOCCA, 89–93.

Thus, the crude beta- or gamma-quinacridone usually undergoes a particle size reduction process. During this particle reduction of the beta or gamma quinacridone, the beta or gamma will tend to convert to the alpha crystal form depending on the milling conditions without a crystal phase inhibitor. As mixing of the alpha-quinacridone with either the beta or gamma phase changes product color shade and decreases heat stability of the final finished pigment, inhibition of this conversion during milling is to be avoided.

EP 517662 and U.S. Pat. No. 5,281,269 describe an aqueous milling process of modifying beta-quinacridone (QA) with base and phase-transfer catalyst.

EP 1020497 describes the color property of the mixed crystal phase pigment with 2,9-dichloroquinacridone.

EP 799863 describes the preparation of beta-phase quinacridone by conversion of alpha-phase quinacridone.

EP 517663 and EP 517662 describe a process of preparing magenta colour beta-1 form quinacridone pigment by either dry milling of beta-quinacridone crude, or milling of beta-quinacridone crude in the presence of water and alcohol.

EP 305328 describes a new magenta color beta-quinacridone that has average particle size over 0.1 microns.

However, none of the above references disclose the use of 2,9-dichloroquinacridone as an alpha-quinacridone crystal phase inhibitor in beta quinacridone particle size reduction process.

Surprisingly, it has been discovered that the beta-quinacridone crystal phase can be preserved during particle size reduction by the addition of 2,9-dichloroquinacridone during the finishing process. The beta-quinacridone product obtained from this process has blue shade violet color that is not achievable when alpha-quinacridone exists in the product.

Furthermore, it has also been discovered that the same crystal phase inhibitor, 2,9-dichloroquinacridone can also be used with the gamma-quinacridone during the particle size reduction to prevent the formation of alpha-quinacridone. Gamma-quinacridone has red color that can be shifted to yellow or bluer shade. Particle size reduction shifts the color to a bluer shade with/without alpha-quinacridone. Beta-quinacridone develops violet color as particle size is reduced. Without alpha-quinacridone, the beta shifts to a bluer violet shade. Thus, a saturated violet color product for beta and red color for gamma is produced with better pigment properties for coatings, plastics and ink applications is achieved for both beta-quinacridone and gamma-quinacridone by milling in the presence of 2,9-dichoroquinacridone as a crystal phase inhibitor.

SUMMARY OF THE INVENTION

The process of the invention is a method of reducing the particle size of crude beta- or gamma-quinacridone pigment crystals while maintaining the beta or gamma crystal phase comprising the steps of combining 2,9-dichloroquinacridone with the crude beta or gamma-quinacridone, wherein the 2,9-dichloroquinacridone added to the crude pigment is about 0.1% to about 5.0 weight % or 0.5% to about 5.0 weight % based on the dry weight of the crude pigment, and milling until the beta or gamma-quinacridone reaches the desired pigmentary particle size.

A second embodiment of the invention encompasses a method of reducing the particle size of beta- or gamma-quinacridone pigment crystals while preventing the beta or gamma crystal phase from converting to the alpha phase comprising the steps of combining 2,9-dichloroquinacridone with the crude beta or gamma-quinacridone, wherein about 0.5% to about 5.0 weight % 2,9-dichlroquinacridone is added to the crude pigment based on the dry weight of the crude pigment and milling until the beta or gamma-quinacridone reaches the desired pigmentary particle size.

The desired pigmentary particle size for the purposes of the invention will vary depending upon the final application. Pigment primary particle size distribution is generally reduced to about 30–300 nm depending on the milling time and size of milling media. Preferably the pigment primary particle size distribution is reduced to about 40–200 nm. Optionally, a re-growth process may be followed in order to achieve the opacity needed for a particular application. The products obtained from this invention process can be transparent, semi-transparent or opaque.

The 2,9-dichloroquinacridone may be a crude pigment or a finished pigment.

The structure of 2,9-dichloroquinacridone used in this invention is described in formula (A).

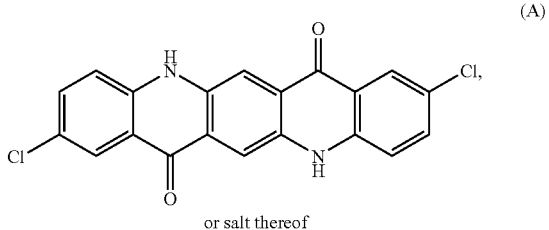

(A) or salt thereof

Beta-quinacridone or gamma-quinacridone crude pigment used in this invention is an unsubstituted quinacridone pigment in the beta or gamma crystal phase as described in formula B.

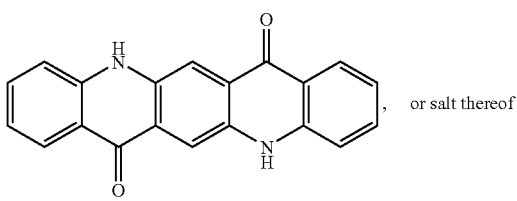

(B) , or salt thereof

BRIEF DESCRIPTION OF THE DRAWINGS

FIG. 1. X-ray of pure alpha quinacridone.

FIG. 2. X-ray of pure beta-quinacridone.

FIG. 3. X-ray of example 1, aqueous wet-milled crude beta-quinacridone without 2,9-dichloroquinacridone.

FIG. 4. X-ray of example 2, aqueous wet-milled crude beta-quinacridone with 2,9-dichloroquinacrione.

FIG. 5. X-ray of example 3, aqueous wet-milled crude beta-quinacridone with 2,9-dichloroquinacridone.

FIG. 6. X-ray of example 4, aqueous wet-milled crude beta-quinacridone with 2,9-dichloroquinacridone.

FIG. 7. X-ray of example 5, aqueous wet-milled crude beta-quinacridone with 2,9-dichloroquinacridone.

FIG. 8. X-ray of comparison example 1.

FIG. 9. X-ray of comparison example 2.

FIG. 10. X-ray of comparison example 3.

FIG. 11. X-ray of unmilled gamma-quinacridone.

FIG. 12. X-ray of aqueous wet-milled gamma crude for 12 minutes.

FIG. 13. X-ray of aqueous wet-milled gamma crude of example 18 with 0.5% 2,9-dichloroquinacridone for 30 minutes.

FIG. 14. X-ray of aqueous wet-milled gamma crude of example 13 with 0.5% 2,9-dichloroquinacridone for 60 minutes.

FIG. 15. X-ray of aqueous wet-milled gamma crude of example 14 with 0.5% 2,9-dichloroquinacridone for 90 minutes.

FIG. 16. X-ray of aqueous wet-milled gamma crude of example 16 with 0.5% 2,9-dichloroquinacridone for 120 minutes.

FIG. 17. X-ray of aqueous wet-milled gamma crude of example 15 with 1.0% 2,9-dichloroquinacridone for 120 minutes.

FIG. 18. X-ray of aqueous wet-milled gamma crude of example 11 with 2.0% 2,9-dichloroquinacridone for 120 minutes.

FIG. 19. X-ray of aqueous wet-milled gamma crude of example 17 with 3.0% 2,9-dichloroquinacridone for 120 minutes.

FIG. 20. X-ray of aqueous wet-milled beta crude of example 6 with 0.5% 2,9-dichloroquinacridone for 60 minutes.

FIG. 21. X-ray of aqueous wet-milled beta crude of example 7 with 0.5% 2,9-dichloroquinacridone for 120 minutes.

FIG. 22. X-ray of aqueous wet-milled beta crude of example 8 with 1.0% 2,9-dichloroquinacridone for 60 minutes.

FIG. 23. X-ray of aqueous wet-milled beta crude of example 9 with 1.0% 2,9-dichloroquinacridone for 120 minutes.

FIG. 24. X-ray of aqueous wet-milled beta crude of example 10 with 2.0% 2,9-dichloroquinacridone for 60 minutes.

DETAILED DESCRIPTION OF THE INVENTION

The crude beta- or gamma-pigments are generally those lacking in properties required for a colorant because of inferior color development and having a particle diameter size range of about 0.2 to 40 μm, preferably 0.3 to 4 μm, most preferably about 1.0–3.0 μm. Alternatively, in the instant invention, commercially available pigments composed of pigment particles with a particle diameter size range of about 0.3 to 0.5 μm may be used as the raw materials to be milled.

In particular, the unsubstituted quinacridones of formula (B) in crude beta and gamma crystal phases are especially preferred.

Aqueous milling may be carried out using known wet-milling methods. Although the particular milling apparatus is generally not critical, suitable mills include horizontal mills, for example, Dyno-mill, Eiger mills, Netzsch mills, and Super mills. Additional vertical mills, ball mills, attritors, vibratory mills, and the like containing various grinding media are suitable. Suitable grinding media include salt, sand, glass beads, ceramic beads and alumina, zirconium or metal beads.

Milling may also be carried out by dispersion milling. A commercial dispersion milling process for quinacridone pigments wherein the particle size thereof is reduced is disclosed in U.S. Pat. No. 3,030,370. The process involves milling in the presence of anhydrous aluminum sulfate and in the presence of a crystallizing solvent. The crystallizing solvents are broadly defined as anhydrous organic solvents with boiling ranges high enough to withstand the heat of grinding without volatilization and low enough to permit removal by steam distillation. Suitable solvents include tetrachloroethylene, other hydrocarbons and chlorinated hydrocarbons and lower alkyl esters of $C_2$–$C_{10}$ dibasic carboxylic acids can also be readily utilized as crystallizing solvents in such dispersion milling processes.

Grinding in the absence of solvents tends to convert the products to the least stable phases (alpha phase). The introduction of a solvent alters the equilibrium but the degree of alteration is influenced by the nature and amount of solvent, the nature of the pigment, and the amount of grinding. The solvent tends to promote the formation of the more stable phases or, as a corollary, to retain the more stable phase if it is the starting material.

Regardless of the type of milling used (wet-milling or dispersion milling), the process of the invention has surprisingly discovered that milling of crude beta- or gamma-quinacridone pigment with 2,9-dichloroquinacridone either maintains the beta or gamma phase and/or prevents the starting beta or gamma phase from converting to the less stable alpha phase.

Milling temperature depends on the size of the mill, and the quantity of crude pigment being milled but is generally carried out at a temperature of 20° C. to about 95° C. Preferably the process milling temperature is 30° C. to about 90° C. Optionally, cooling with water may control the temperature.

In the instant invention, the average particle diameter of the resulting milled pigments are about 30–300 nm, preferably 40–200 nm.

Particle size reduction time for either the beta-quinacridone or gamma-quinacridone in the presence of the crystal phase inhibitor, 2,9-dicholorquinacridone may vary from thirty minutes to forty-eight hours depending upon the particle size needed for a particular application and the particular crude pigment being wet-milled or dispersion milled.

Grinding media for wet-milling is generally loaded to about 75%–85% of chamber space. The milling media, consists of beads composed of materials such as zirconium oxide, glass, borosilicate, metal, alumina and polymeric beads for example, those described in U.S. Pat. Nos. 5,902, 711, and 5,478,705.

Grinding media for dispersion milling is generally steel shot, iron nails and spikes, or ceramic beads. Dispersion milling cycles generally range from about 2 to about 48 hours. The amount of solvent is chosen such that the desired crystal phase is maintained, while allowing the desired particle size to be generated in a reasonable mill time. Amounts ranging from 2 to 15%, by weight of quinacridone, and preferably 4 to 13%, are generally utilized.

Suitable milling liquid for wet-milling is water, and can include less than 5 wt. % of polar organic solvent, such as dimethylformamide, dimethylacetamide, dimethylsulfoxide, lower aliphatic alcohols such as methanol, ethers including tetrahydrofuran and dioxane, and alkylene glycols and triols such as ethylene glycol and glycerol.

The wet-milling liquid is made up of greater than about 10 wt. % water, preferably greater than about 20 wt. % water, and most preferably greater than 30 wt. % water. For example, water makes up about 5 wt. % to about 98 wt. %, 60 wt. % to about 95 wt % based on the total milling composition. Thus the crude quinacridone makes up about 2 wt. % to about 75 wt. %, for example about 5 wt. % to about 30 wt. % or about 2 wt. % to about 20 wt % of the total weight of the milling composition.

The milling may take place at a pH that ranges from about 4.0 to about 12.0. The pH is preferably about 6 to about 9.

The dispersion-milling may be carried out in an appropriate crystallizing solvent. The crystallizing solvents are broadly defined as anhydrous organic solvents with boiling ranges high enough to withstand the heat of grinding without volatilization and low enough to permit removal by steam distillation. Suitable solvents include tetrachloroethylene, other hydrocarbons and chlorinated hydrocarbons and lower alkyl esters of $C_2$–$C_{10}$ dibasic carboxylic acids can also be readily utilized as crystallizing solvents in such dispersion milling processes.

Colored additives, such as organic pigment derivatives, or uncoloured additives, such as polymers, can also optionally be added to the milling mixture during the milling process.

The crude pigment may be optionally wet-milled or dispersion milled with other additives such as surface modification reagents, rheology improving agents, texture improving agents, defoamers, wetting agents, particle growth inhibitors, other crystal phase directors, antiflocculants, polymeric wet-milling aids and dispersants.

Surface modifying reagents, rheology improving agents and texture improving agents may include quinacridone monosulfonic acid or quinacridone monosulfonic acid aluminum salt, 3,5-dimethylpyrazol-1-methyl quinacridone or phthalimidomethyl quinacridone. Other suitable texture improving agents are, in particular, fatty acids of not less than 18 carbon atoms, for example stearic or behenic acid or their amides or metal salts thereof, preferably sodium or ammonium salts, as well as plasticizers, waxes, resin acids such as abietic acid or metal salts thereof, colophonium, alkyl phenols or aliphatic alcohols such as stearyl alcohol or vicinal diols such as dodecane-1,2-diol. The additives may be added directly to the milling slurry or at the same time as the crude pigment. The additive or additives may optionally be added at about 0.5–20.0 wt. % based on the dry weight of the crude organic pigment. Preferably the additive or additives are optionally added at about 1.0–5.0 wt. % based on the dry weight of the crude organic pigment.

Defoamers can be used optionally in the inventive wet-milling process. The defoamer may be added before and/or during milling for foam control.

Dispersing agents or polymeric grinding aids for wet-milling may be styrenic resins such as those described in copending U.S. application Ser. No. 60/519,842 or acrylic resins such as those described in U.S. Pat. No. 6,410,619.

After milling, the pigment may be separated from the milling mixture by one or more isolation methods known in the art. Filtration, followed by washing to remove residual salts and solvent, is the preferred separation method. Other collection methods known in the art, such as tray drying, spray drying, spin flash drying, lyophilization, centrifugation, or simple decantation are also suitable isolation methods. Such methods can be used individually or in combination.

The present reduced size gamma and/or beta quinacridone pigments are suitable as coloring matter for inorganic or organic substrates. They are highly suitable for coloring high molecular weight materials, which can be processed to casted and molded articles or which are used in ink and coating compositions such as solvent or water based coatings, for example in automotive coatings. Preferred high molecular weight materials are plastics that are subsequently calendered, cast, molded or processed to fibers and industrial or automotive paints or ink coatings.

For the purposes of the invention, high molecular weight material is defined as material in the range of $10^3$ to $10^8$ g/mol.

Suitable high molecular weight organic materials include thermoplastics, thermoset plastics or elastomers, for example, cellulose ethers; cellulose esters such as ethyl cellulose; linear or crosslinked polyurethanes; linear, crosslinked or unsaturated polyesters; polycarbonates; polyolefins such as polyethylene, polypropylene, polybutylene or poly-4-methylpent-1-ene; polystyrene; polysulfones; polyamides; polycycloamides; polyimides; polyethers; polyether ketones such as polyphenylene oxides; and also poly-p-xylene; polyvinyl halides such as polyvinyl chloride, polyvinylidene chloride, polyvinylidene fluoride or polytetrafluoroethylene; acrylic and methacrylic polymers such as polyacrylates, polymethacrylates or polyacrylonitrile; rubber; silicone polymers; phenol/formaldehyde resins; melamine/formaldehyde resins; urea/formaldehyde resins; epoxy resins; diene rubbers or copolymers thereof such as styrene butadiene rubber; acrylonitrile-butadiene rubber or chloroprene rubber; singly or in mixtures.

Generally, the present reduced size gamma and/or beta quinacridone pigments are used in an effective pigmenting amount, for example, of 0.01 to 30% by weight, preferably 0.1 to 10% by weight, based on the weight of the high molecular weight organic material to be pigmented. Thus, the present invention also relates to a pigmented plastic composition, which comprises a plastic material and an effective pigmenting amount of a pigment or pigment solid solution prepared according to a process of the present invention, and to a process for preparing said pigmented plastic compositions.

The present present reduced size gamma and/or beta quinacridone pigments are easily dispersible and can be readily incorporated into organic matrixes to provide homogenous colorations possessing high saturation.

The high molecular weight organic materials are pigmented with the present reduced size gamma and/or beta quinacridone pigments by mixing the pigments, if desired in the form of a masterbatch, into substrates using high shear techniques including roll mills or a mixing or grinding apparatus. The pigmented material is then brought into the desired final form by known methods, such as calandering, pressing, extruding, brushing, casting or injection molding.

EXAMPLES

General Wet-Milling Procedure

The aqueous particle size reduction process (wet-milling) for the crude beta-quinacridone is performed using circulation milling media, such as zirconium oxide beads in a Netzsch-mill and Dyno-mill, in a size range of about 0.2–1.2 mm diameter with a loading of about 75 to about 90% of milling chamber space. Other than water, the milling slurry has a composition of about 5 to about 45% organic pigment or mixture of pigments based on the total weight of the slurry. Optionally, the milling media may have about 0.5 to about 20% pigment derivative additives, based on the dry weight of the pigment, non-pigment additives including polymeric dispersants or mixtures of additives. Particle size reduction time may vary from about ten minutes to about forty-eight hours in order to achieve the particle size needed for the application. Milled product may be isolated after particle size reduction process, or the crystal size can be re-grown by heating the aqueous slurry to about 70 to about 95° C. with addition of base, polar organic solvent and/or amine salt.

General Dispersion Milling Procedure

The disperson milling process for the crude gamma or beta-quinacridone is preformed by charging a commercial ball mill with "Cyl-Pebs®" (approximately 2.5 cm sections of 1.6 cm diameter steel rod) and railroad spikes along with commercial aluminum sulfate and a crystallizing solvent. In the present example the crystallizing solvent is dimethyl glutarate. The crude gamma or beta-quinacridone is then charged into the ball mill. The charge is ground by rotating the mill for about 2 to about 48 hours. The contents of the mill are then discharged through a screen which retains the "Cyl-Pebs®" and railroad spikes.

Extraction after dispersion milling of beta or gamma-quinacridone.

A suitable vessel is charged with 1.5% sulfuric acid and the milled content above. The mixture is heated to about 90° C. The pigmentary solution of gamma-quinacridone is isolated in a suitable filtration device and washed free of acid and salts. The resulting water wet pigment may be either dried or further treated depending on the desired end use.

Color data is obtained using CM-3600d spectrophotometer manufactured by Minolta Corporation USA. 101 Williams Drive, Ramsey, N.J.

Beta-Quinacridone

Example 1

Crude Beta-Quinacridone Aqueous Milling with Phthalimidomethyl Quinacridone, without 2,9-dichloroquinacridone To a 5000 ml circulation flask is added 200.0 g of dry beta-quinacridone crude, 32.0 g of polymeric dispersant Scripset 720 (25% maleic acid acrylic acid copolymer in water) manufactured by Hercules Incorporated, Wilmington, Del., 8.0 g phthalimidomethyl quinacridone, and 500.0 g of water. Above chemicals are mixed with a mechanic stirrer for 30 minutes. The resulting slurry is milled in a Netzsch Mill in a pH range of 7.0–9.0.

The Netzsch Mill grinding chamber is filled with 1825.0 g (500 ml) of 0.3 mm $ZrO_2/Y_2O_3$ beads and 367.0 g of water. Prepared pigment slurry is pumped into the Netzsch Mill, milling is started at flow rate of 400.0 g/minute, tip speed set up at 12.0M/minute, and milling temperature is controlled in a range of 50–55° C. Total milling time is 120 minutes. Milled beta-quinacridone slurry is diluted with 500.0 g of water, slurry pH is adjusted to 5.0 with 2% $H_2SO_4$, then filtered and washed with hot water till pH 7.0, dried in an oven at 80° C. The isolated product is submitted for screening in alkyd melamine paint. X-ray of the milled product shows a peak at 14θ corresponding to alpha-quinacridone. Color data of beta-quinacridone crude and the milled product is listed in Table 3. X-ray of the milled crude beta-quinacridone without 2,9-dichloroquinacridone product is shown FIG. 3.

Example 2

Crude Beta-Quinacridone Aqueous Milling with Phthalimidomethyl Quinacridone and 2,9-dichloroquinacridone To a 5000 ml circulation flaks is added 171.5 g of dry beta-quinacridone crude, 3.5 g of phthalimidomethyl quinacridone, 3.5 g of 2,9-dichloroquinacridone, and 1951.5 g of water. Above chemicals are mixed with a mechanic stirrer for 30 minutes. The resulting slurry is milled in a Netzsch Mill in a pH range of 7.0–9.0.

The Netzsch Mill grinding chamber is filled with 1825.0 g (500 ml) of 0.3 mm $ZrO_2/Y_2O_3$ beads and 370.0 g of water. Prepared pigment slurry is pumped into the Netzsch Mill, milling is started at flow rate of 800.0 g/minute, tip speed set up at 12.0M/minute, and milling temperature is controlled in a range of 80–85° C. Total milling time is 102 minutes. 500.0 g of milled beta-quinacridone slurry is diluted with 500.0 g of water, then filtered and washed with hot water till pH 7.0, dried in an oven at 80° C. The isolated product is submitted for screening in alkyd melamine paint. X-ray of the milled product shows no peak at 14θ, which indicates no alpha-quinacridone. Color data of the milled product is listed in Table 3. X-ray of the milled product is shown in FIG. 4.

Example 3

Crude Beta-Quinacridone Aqueous Milling with 2,9-dichloroquinacridone

To a 5000 ml circulation flaks is added 171.5 g of dry beta-quinacridone crude, 3.5 g of 2,9-dichloroquinacridone 14.0 g of Staybelite Ester®, a polymeric dispersant 10–55WK (55% active aqueous dispersion of the glycerol ester of hydrogenated rosin mixture, manufactured by Eastman Chemical Resins, Kingsport, Tenn.), and 1955.0 g of water. Above chemicals are mixed with a mechanic stirrer for 30 minutes. The resulting slurry is milled in a Netzsch Mill in a pH range of 7.0–9.0.

The Netzsch Mill grinding chamber is filled with 1825.0 g (500 ml) of 0.3 mm $ZrO_2/Y_2O_3$ beads and 370.0 g of water. Prepared pigment slurry is pumped into the Netzsch Mill. Milling is started at flow rate of 800.0 g/minute, tip speed set up at 12.0M/minute, and milling temperature is controlled in a range of 80–85° C. Total milling time is 60 minutes. 300.0 g of milled beta-quinacridone slurry is diluted with 500.0 g of water, then filtered and washed with hot water till pH 7.0, dried in 80° C. oven overnight. The isolated product is submitted for screening in alkyd melamine paint. X-ray of the milled product shows no peak at 14θ, which indicates no alpha-quinacridone. Color data of the milled product is listed in Table 3. X-ray of the milled product is shown in FIG. 5.

Example 4

Crude Beta-Quinacridone Aqueous Milling with 2,9-dichloroquinacridone.

Example 3 is repeated except; milling time is 90 minutes. The isolated product is submitted for screening in alkyl melamine paint. X-ray of the milled product shows no peak at 14θ, which indicates no alpha-quinacridone. Color data of the milled product is listed in Table 3. X-ray of the milled product is shown in FIG. 6.

Example 5

Crude Beta-Quinacridone Aqueous Milling with 2,9-dichloroquinacridone.

Example 3 is repeated except; milling time is 120 minutes. The isolated product is submitted for screening in alkyd melamine paint. X-ray of the milled product shows no peak at 14θ, which indicates no alpha-quinacridone. Color data of the milled product is listed in Table 3. X-ray of the milled product is shown in FIG. 7.

Example 6–11

Example 3 is repeated for examples 6–11 except; milling time is varied, amount of 2,9-dichloroquinacridone is also varied and no Staybelite Ester® is added. See FIGS. 20–24. X-rays of the milled products shows no peak at 14θ. Thus 2,9-dichloroquinacridone functions as an alpha phase inhibitor at varying dosage levels and varying milling times.

TABLE 1

| Example (beta-crude milling) | Milling time in minutes | 2,9-dichloroquinacridone in wt. % | Method of Milling |
|---|---|---|---|
| 6 | 60 | 0.5 | Wet-milling |
| 7 | 120 | 0.5 | Wet-milling |
| 8 | 60 | 1.0 | Wet-milling |
| 9 | 120 | 1.0 | Wet-milling |
| 10 | 60 | 2.0 | Wet-milling |
| 11 | 120 | 2.0 | Wet-milling |

Gamma-Quinacridone

Example 12

To a dispersion mill 100 lbs Cylpebs® and 10 lbs of spikes is charged followed by a charge of 1532.2 grams aluminum sulfate (anhydrous), 647.1 grams crude gamma quinacridone, 20.4 grams 4,11-dichloroquinacridone, 13.6 grams 2,9-dichloroquinacridone, and 18.7 grams dimethylglutarate. Grinding continues at 40 rpm for 5 hours.

The mill powder is extracted with sulfuric acid and water (1.5% sulfuric acid) with stirring for 2 hr at 90° C. Water is then added to cool the extraction mixture to about 60 to about 65° C., with filtering and washing to neutral pH. The finished gamma-quinacridone is dried to less than 1% moisture before formulation with alkyl melamine paint and testing to determine color space in table 5.

When crude gamma-quinacridone is dispersion milled with 2,9-dichloroquinacridone, then extracted as above, the gamma phase is preserved. See color space in table 5 for example 12.

Example 13–18

Crude Gamma-Quinacridone Aqueous Milling with 2,9-dichloroquinacridone

Example 3 is repeated in examples 13–18 except no Staybelite Ester® was added and the crude pigment milled is gamma-quinacridone. The milling times and amounts of 2,9 dichloroquinacridone added during wet-milling are varied as in Table 2 below. Table 5 below shows color data.

TABLE 2

| Example | Milling time in minutes | 2,9-dichloroquinacridone in wt. % | Method of Milling |
|---|---|---|---|
| 12 | 120 | 2.0 | Dispersion milling and extraction |
| 13 | 60 | 0.5 | Wet-milling |
| 14 | 90 | 0.5 | Wet-milling |
| 15 | 120 | 1.0 | Wet-milling |
| 16 | 120 | 0.5 | Wet-milling |
| 17 | 120 | 3.0 | Wet-milling |
| 18 | 30 | 0.5 | Wet-milling |

Milling with 2,9-dichloroquinacriodone directs the gamma-quinacridone to beta and/or alpha, depending on the amount of 2,9-dichloroquinacridone. When the gamma crude is milled with 0.5% 2,9-dichloroquinacridone for a maximum of 2 hours the gamma is converted to beta crude predominantly. See X-ray FIG. 16. As the amount of 2,9-dichloroquinacridone is increased from 1.0% to 3% 2,9-dichloroquinacridone, the amount of alpha conversion increases. Thus the gamma crude milling in the presence of 2,9-dichloroquinacridone directs the crude gamma predominantly to beta when dosages of approximately 0.5 wt. % or less of 2,9-dichloroquinacidone are used as an additive. Predominantly means for the purposes of the invention, that greater than about 85% of the gamma crude is converted to beta, preferably about 90% of the gamma crude is converted to beta phase.

Comparison examples are prepared in order to examine X-ray pattern of alpha-quinacridone and beta-quinacridone mixture. Samples are generated by physical mixing the known beta-quinacridone and alpha-quinacridone in a given percentage, X-ray spectra are obtained.

Comparison Example 1

To a 100 mL solid sample bottle is added 0.250 g of alpha-quinacridone obtained from milling process, and 2.0 g of beta-quinacridone crude, alpha-quinacridone and beta-quinacridone weight ratio equals 1.0/8.0. Above sample is placed in a shaker and mixes for 60 minutes before submitting for X-ray. A peak at 14θ is corresponding to alpha-quinacridone. X-ray spectrum is shown in FIG. 8.

Comparison Example 2

To a 100 mL solid sample bottle is added 0.600 g of alpha-quinacridone obtained from milling process, and 2.0 g of beta-quinacridone crude, alpha-quinacridone and beta-quinacridone weight ratio equals 1.0/3.3. Above sample is placed in a shaker and mixes for 60 minutes before submitting for X-ray. A peak at 14θ corresponds to alpha-quinacridone. X-ray spectrum is shown in FIG. 9.

Comparison Example 3

To a 100 mL solid sample bottle is added 1.0 g of alpha-quinacridone obtained from milling process, and 1.0 g of beta-quinacridone crude, alpha-quinacridone and beta-quinacridone weight ratio equals 1/1. Above sample is placed in a shaker and mixes for 60 minutes before submitting for X-ray. A peak at 14θ corresponding to alpha-quinacridone. X-ray spectrum is shown in FIG. 10.

Color of Aqueous Milled Beta-Quinacridone vs. Crude in Alkyd/Melamine Paint[a]

|  | Tint | Color | | | Masstone | Color | | |
|---|---|---|---|---|---|---|---|---|
| Sample | L | C | H | Str. | L | C | H | Trans. |
| Crude β-quinacridone | 69.9 | 18.6 | 337.5 | 100.0 | 38.5 | 44.3 | 9.7 | STD |
| Example 1 | 62.0 | 28.5 | 326.7 | 224.9 | 35.0 | 40.5 | 6.2 | +3.7 |
| Example 2 | 61.3 | 27 | 322.2 | 353.9 | 34.3 | 36.8 | 9.0 |  |
| Example 3 | 62.2 | 25.3 | 324.6 | 354.9 | 34.7 | 37.6 | 9.3 |  |
| Example 4 | 62.1 | 25.1 | 323.9 | 357.9 | 34.5 | 37.0 | 8.8 |  |
| Example 5 | 61.7 | 25.4 | 323.3 | 357.9 | 34.4 | 36.6 | 8.8 |  |

TABLE 4

|  | Tint | Color | | | Masstone | Color | | |
|---|---|---|---|---|---|---|---|---|
| Sample | L | C | H | Str. | L | C | H | Trans. |
| Commercial beta-Violet | 60.4 | 28.5 | 321.9 | 100.0 | 33.6 | 34.2 | 8.9 | STD |
| Example 6 | 61.4 | 27.0 | 326.7 | 92.0 | 35.6 | 36.2 | 9.1 | −7.3 |
| Example 7 | 61.6 | 25.9 | 324.9 | 90.0 | 35.2 | 37.0 | 8.6 | −6.5 |
| Example 8 | 61.4 | 27.3 | 325.4 | 94.0 | 35.4 | 37.9 | 8.3 | −5.6 |
| Example 9 | 61.6 | 26.5 | 323.9 | 92.0 | 35.1 | 37.2 | 7.8 | −4.9 |
| Example 10 | 61.2 | 27.6 | 325.6 | 94.0 | 35.3 | 38.1.6 | 8.7 | −5.4 |
| Example 11 | 61.3 | 26.4 | 323.3 | 93.0 | 34.8 | 36.6 | 8.4 | −4.4 |

Color of Aqueous Milled gamma-quinacridone vs. Standard gamma-quinacridone in Alkyd/Melamine Paint[a]

TABLE 5

|  | Tint | Color | | | Masstone | Color | | |
|---|---|---|---|---|---|---|---|---|
| Example | L | C | H | Str. | L | C | h | Trans. |
| Commercial gamma Red | 62.5 | 46.2 | 352.9 | 100.0 | 41.2 | 53.0 | 21.8 | STD |
| Example 12 (dispersion milling and extraction) | 62.6 | 45.5 | 353.1 | 99 | 41.8 | 54.5 | 22.0 | −0.8 |
| Example 13 | 62.9 | 46.2 | 354.5 | 104.0 | 42.2 | 54.5 | 22.2 | −7.6 |
| Example 14 | 63.4 | 47.4 | 355.4 | 103.0 | 43.0 | 55.2 | 22.7 | −2.1 |
| Example 15 | 60.3 | 41.6 | 345.8 | 105.0 | 36.6 | 43.2 | 14.8 | 3.5 |
| Example 16 | 55.3 | 28.6 | 326.7 | 154.0 | 32.6 | 28.4 | 4.9 | 1.2 | a. Alkyl Melamine Paint Formulation:
  Millbase:
    To a 8 oz jar is added 1.2 g of pigment sample, 0.6 g of disperbyk 161 (high molecular weight block co-polymer dispersing additive, 30% active), 56.2 g of alkyd melamine resin, 100 g glass beads (ø2 mm). Above mixture is placed in a Skandex and milled for 2 hours. Pigment slurry is separated form glass beads, and collected as millbase. Pigment percentage is 2.1%.
  Masstone Color:
    7.5 g of above millbase is diluted with 22.5 g of alkyd melamine resin, the pigment dispersion is drawn down on a Black/White Carton with 100 μm wet film wired bar coater (No. 8) with the KCC automatic film applicator, dried 30 minutes @130° C.
  Tint Color:
    16.7 g of above millbase is diluted with 15.0 g of white paint (20% $TiO_2$), the pigment dispersion is drawn down on a White Card with 100 μm wet film wired bar coater (No. 8) with the KCC automatic film applicator, dried 30 minutes @130° C.

We claim:
1. A process of reducing the particle size of a crude quinacridone pigment, wherein the pigment is in a beta crystal phase, while maintaining the said beta-crystal phase comprising the steps of
    combining a milling composition comprising 2,9-dichloroquinacridone with the crude quinacridone pigment,
      wherein the wt. % of the 2,9-dichloroquinacridone is about 0.1% to about 5.0 weight % based on the dry weight of the pigment, and
milling to reduce the particle size of said pigment, wherein the crude quinacridone makes up about 2 wt. % to about 75 wt. % of the total weight of the milling composition.

2. A process according to claim 1, wherein the crude pigment is wet-milled or dispersion milled.

3. A process according to claim 1, wherein the crude beta pigment is wet-milled.

4. A process according to claim 1, wherein the crude beta pigment is dispersion milled.

5. A process according to claim 1, wherein the crude pigment has a particle size range of about 0.3 μm to about 4.0 μm.

6. A process according to claim 1, wherein the particle size after milling about 30 nm to about 300 nm.

7. A process according to claim 1, wherein the crude pigment is milled in the presence of one or more other additives selected from the group consisting of modification reagents, rheology improving agents, texture improving agents, defoamers, wetting agents, particle growth inhibitors, crystal phase directors, antiflocculants, polymeric milling aids and dispersants.

8. A process according to claim 3, wherein the composition after milling shows a maximum wt. % of about 5 wt. % alpha-quinacridone based on the dry weight of the milled composition.

9. A process according to claim 7 wherein the crude quinacridone is about 5 wt % to about 30 wt. % based on the total weight of the milling composition.

10. A process according to claim 1, wherein the milling composition contains water.

11. A process according to claim 10, wherein the water makes up about 5 wt. % to about 98 wt. % based on the total milling composition.

12. A process according to claim 11, wherein the water makes up about 60 wt. % to about 95 wt. % based on the total milling composition.

13. A process according to claim 9, wherein the crude quinacridone makes up about 2 wt. % to about 20 wt. % of the total milling composition.

14. A process according to claim 1, wherein the process takes place at a pH from about 4.0 to about 12.0.

15. A process according to claim 1, wherein the process further includes at least one of the steps selected from the group consisting of isolation, crystal re-growth and surface treatment.

16. A high molecular weight organic material having incorporated therein the reduced size quinacridone according to the process of claim 1, wherein high molecular weight material is defined as material in the range of $10^3$ to $10^8$ g/mol.

17. A material according to claim 16, wherein the material is an ink, coating or plastic.

18. A process for coloring a high molecular weight organic material, which comprises incorporating an effective pigmenting amount of the reduced size quinacridone obtained according to the process of claim 1 into a high molecular weight organic material and the high molecular weight organic material is defined as material in the range of $10^3$ to $10^8$ g/mol.

* * * * *

UNITED STATES PATENT AND TRADEMARK OFFICE
CERTIFICATE OF CORRECTION

PATENT NO. : 7,101,428 B2  Page 1 of 1
APPLICATION NO. : 10/988227
DATED : September 5, 2006
INVENTOR(S) : Yingxia He et al.

It is certified that error appears in the above-identified patent and that said Letters Patent is hereby corrected as shown below:

On the title page
[60] should read:

Related U.S. Application Data

-- [60] This application is a continuation-in-part of Application No. 10/988,250, filed on November 12, 2004, now U.S. Patent No. 7,122,081 which claims benefit of U.S. Provisional Application No. 60/519,842, filed on November 13, 2003. --.

Column 1
Paragraph 1 should read:

-- This application is a continuation-in-part of Application No. 10/988,250, filed on November 12, 2004, now U.S. Patent No. 7,122,081 which claims benefit of U.S. Provisional Application No. 60/519,842, filed on November 13, 2003. --.

Signed and Sealed this

Fifth Day of June, 2007

JON W. DUDAS
*Director of the United States Patent and Trademark Office*